(12) United States Patent
Sawanoi et al.

(10) Patent No.: US 11,464,415 B2
(45) Date of Patent: Oct. 11, 2022

(54) SPHYGMOMANOMETER

(71) Applicant: OMRON HEALTHCARE Co., Ltd., Muko (JP)

(72) Inventors: Yukiya Sawanoi, Kyoto (JP); Miki Imamura, Kyoto (JP)

(73) Assignee: OMRON HEALTHCARE Co., Ltd., Muko (JP)

( * ) Notice: Subject to any disclaimer, the term of this patent is extended or adjusted under 35 U.S.C. 154(b) by 110 days.

(21) Appl. No.: 16/904,901

(22) Filed: Jun. 18, 2020

(65) Prior Publication Data

US 2020/0315472 A1 Oct. 8, 2020

Related U.S. Application Data

(63) Continuation of application No. PCT/JP2018/044740, filed on Dec. 5, 2018.

(30) Foreign Application Priority Data

Jan. 10, 2018 (JP) .............................. JP2018-002070

(51) Int. Cl.

| A61B 5/021 | (2006.01) |
| A61B 5/022 | (2006.01) |
| A61B 5/0225 | (2006.01) |
| A61B 5/0235 | (2006.01) |
| A61B 5/00 | (2006.01) |

(52) U.S. Cl.
CPC ........ *A61B 5/02225* (2013.01); *A61B 5/0225* (2013.01); *A61B 5/0235* (2013.01); *A61B 5/02141* (2013.01); *A61B 5/743* (2013.01); *A61B 2562/0247* (2013.01)

(58) Field of Classification Search
CPC ....... A61B 5/02; A61B 5/022; A61B 5/02225; A61B 5/742; G06F 3/0485
See application file for complete search history.

(56) References Cited

FOREIGN PATENT DOCUMENTS

| CN | 2882529 Y | 3/2007 |
| JP | H09-257522 A | 10/1997 |
| JP | 2007-135717 A | 6/2007 |

(Continued)

OTHER PUBLICATIONS

Espacenet Translation of JP 2007135717A retrieved on Dec. 18, 2021 (Year: 2007).*

(Continued)

*Primary Examiner* — Christian Jang
(74) *Attorney, Agent, or Firm* — Maier & Maier, PLLC (57) ABSTRACT

A sphygmomanometer includes a frame that spatially demarcates a region in which a display screen is displayed. On the display screen, a scale indication for making a value of pressure readable is displayed along one direction. On the display screen, a mark that represents a pressure of a cuff by a position of the mark with respect to the scale indication is displayed. When the pressure changes, a display control unit performs control to slide the scale indication with respect to the frame along the one direction at a slide speed corresponding to a predetermined pressure change rate or a pressure change rate obtained by actual measurement in a pressurizing process or a depressurizing process of the cuff so that the mark falls within the frame.

9 Claims, 9 Drawing Sheets

INITIAL STAGE                    CUFF PRESSURE IS INCREASED (56) References Cited

FOREIGN PATENT DOCUMENTS

JP          2007135717 A   *   6/2007

OTHER PUBLICATIONS

Notification of Transmittal of Translation of the International Preliminary Report on Patentability dated Jul. 23, 2020, in connection with corresponding international Application No. PCT/JP2018/044740 (6 pp.).
Translation of International Search Report dated Feb. 5, 2019 in corresponding International Application No. PCT/JP2018/044740; 2 pages.

* cited by examiner

SPHYGMOMANOMETER

CROSS-REFERENCE TO RELATED APPLICATION

This is a continuation application of International Application No. PCT/JP2018/044740, with an International filing date of Dec. 5, 2018, which claims priority of Japanese Patent Application No. 2018-002070 filed on Jan. 10, 2018, the entire content of which is hereby incorporated by reference.

FIELD

The present disclosure relates to a sphygmomanometer, and more particularly, to a sphygmomanometer that electronically displays the pressure of a blood pressure measurement cuff on a display screen as a graph.

BACKGROUND

Manufacture, import and export of equipment using mercury, such as a mercury column sphygmomanometer, will be prohibited in principle in or after 2020 (Minamata Convention on Mercury). Therefore, sphygmomanometers that electronically display a graph imitating a mercury column have attracted attention. For example, Patent Literature 1 (JP 2007-135717 A) discloses a sphygmomanometer including an analog indicator for indicating a measured value of pressure in a cuff as a column graph. This analog indicator has a plurality of segments, each of which corresponds to a pressure amount of 1 mmHg or 2 mmHg, arranged along a scale from 0 mmHg to 300 mmHg.

SUMMARY

However, in the sphygmomanometer of Patent Literature 1, since the entire range of the scale from 0 mmHg to 300 mmHg is fixed and displayed on the indicator, there is a problem that the resolution of indication is as coarse as 1 mmHg or 2 mmHg for the large size of the display screen (size in the longitudinal direction).

Thus, an object of the present disclosure is to provide a sphygmomanometer that can electronically display the pressure of the blood pressure measurement cuff on a display screen as a graph and furthermore can improve the resolution of indication.

In order to achieve the above object, a sphygmomanometer according to the present disclosure is a sphygmomanometer electronically displaying as a graph a pressure of a blood pressure measurement cuff pressing a measurement site on a display screen, the sphygmomanometer comprising:
- a frame that spatially demarcates a region in which the display screen is displayed;
- a scale indication displayed along one direction on the display screen so as to make a value of pressure readable;
- a mark displayed on the display screen so as to represent a pressure of the cuff by a position of the mark with respect to the scale indication; and
- a display control unit configured to perform control to slide the scale indication with respect to the frame along the one direction at a slide speed corresponding to a predetermined pressure change rate or a pressure change rate obtained by actual measurement in a pressurizing process or a depressurizing process of the cuff so that the mark falls within the frame when the pressure changes.

DETAILED DESCRIPTION

Hereinafter, an embodiment of the present disclosure will be described in detail with reference to the drawings.

Figure 1:
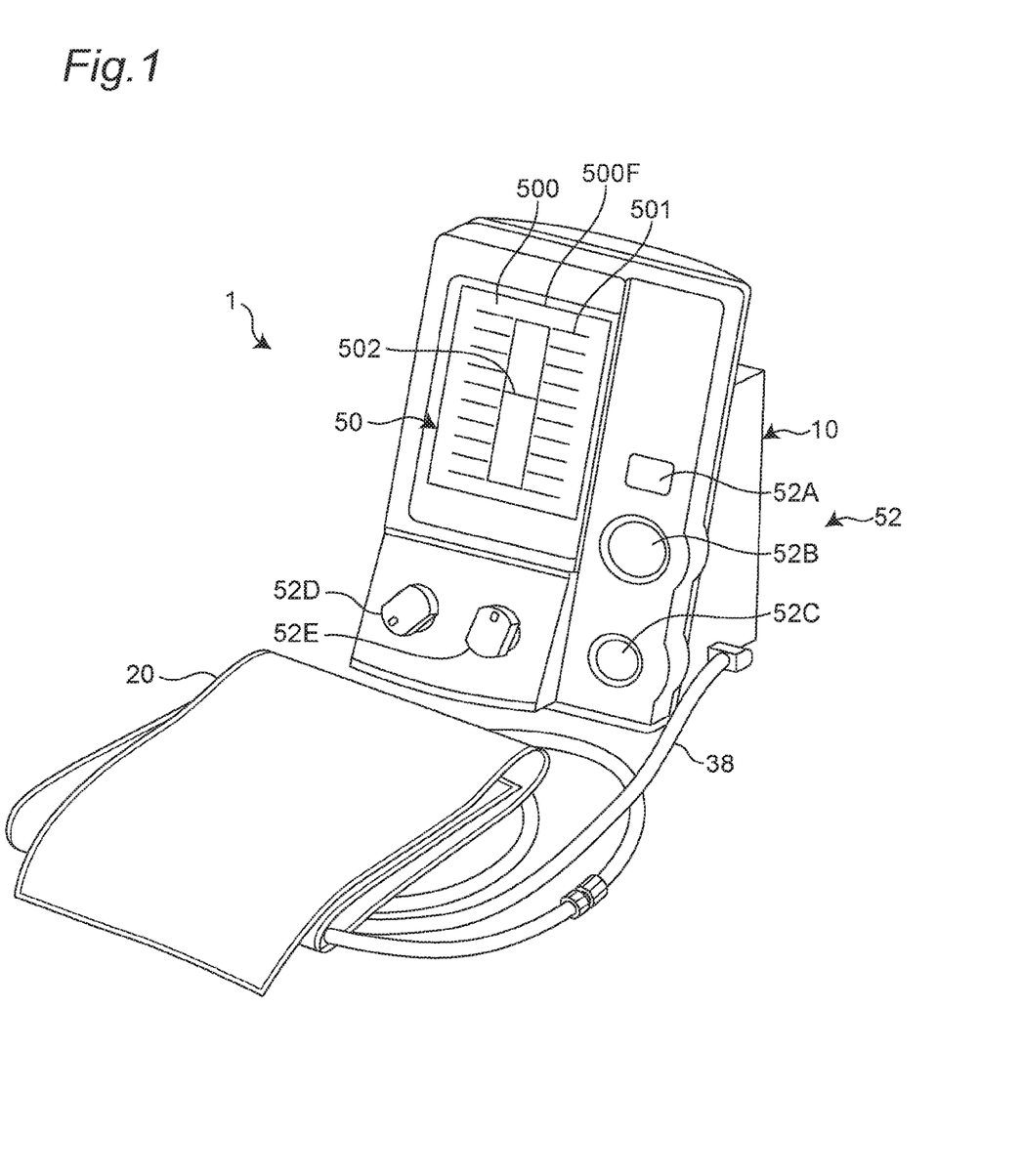
FIG. 1 is a perspective view showing an external appearance of an electronic sphygmomanometer (hereinafter, simply referred to as "sphygmomanometer") according to an embodiment of the present disclosure.

FIG. 1 shows an external appearance of a sphygmomanometer (the whole is denoted by reference numeral 1) according to one embodiment of the present disclosure. The sphygmomanometer 1 includes a blood pressure measurement cuff 20 to be worn on an upper arm of a person to be measured, a main body 10 having a self-standing type, and a flexible air tube 38 that connects the cuff 20 and the main body 10. The cuff 20 contains a fluid bag 22 (see FIG. 2) for pressing the upper arm. An indicator 50 and an operation unit 52 are provided on the front surface of the main body 10.

Figures 5A, 5B:
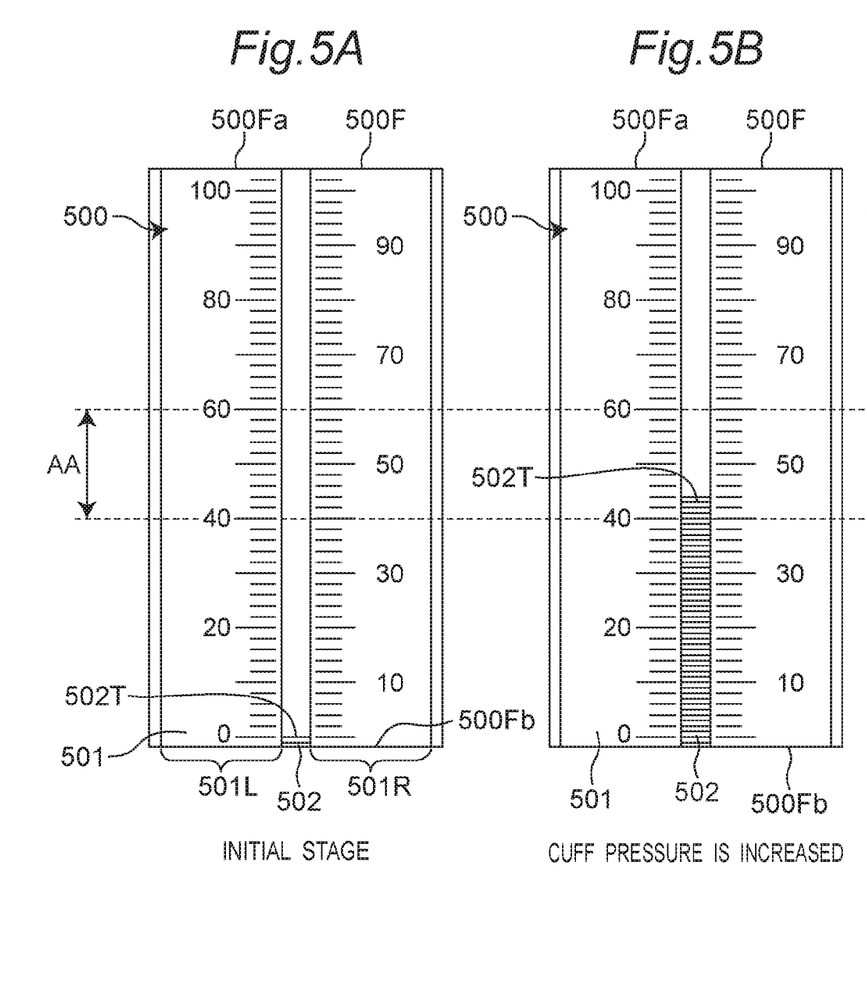
FIG. 5A is a diagram exemplifying a mode in which the display contents of the indicator of the sphygmomanometer change.
FIG. 5B is a diagram exemplifying a mode in which the display contents of the indicator of the sphygmomanometer change.

The indicator 50 includes a liquid crystal display element (LCD) in this example, and according to a control signal from a central processing unit (CPU) 100 as a control unit described below (see FIG. 2), electronically performs a display as a graph, and another display related to blood pressure measurement, on the display screen 500. In this example, the region in which the display screen 500 is displayed is spatially demarcated by a frame 500F having an elongated rectangular frame shape in one direction (longitudinal direction in this example). In this example, the display screen 500 displays a scale indication 501 along the longitudinal direction, and displays a column graph 502 forming a mark along the scale indication 501. The scale indication 501 is slid along the longitudinal direction with respect to the frame 500F as described below, and makes the value of the pressure of the cuff 20 (fluid bag 22) (hereinafter, referred to as "cuff pressure Pc") readable. The column graph 502 indicates the pressure Pc of the cuff 20 with the position of a top portion 502T with respect to the scale indication 501. Specifically, as shown in FIG. 5A, in this example, the column graph 502 is displayed in the center of the display screen 500 (frame 500F), and the scale indication 501 is divided into two left and right portions SOIL and 501R and displayed on both sides of this column graph 502. As a result, the external appearance of the display screen 500 is substantially the same as that of a traditional mercury column sphygmomanometer. Therefore, a user accustomed to using the traditional mercury column sphygmomanometer has a less sense of discomfort when using the sphygmomanometer 1.

The pressure range indicated by the scale indication 501 displayed within the frame 500F corresponds to a range of about 100 mmHg being a part within the range from the minimum indication 0 mmHg to the maximum indication 300 mmHg. In the example in FIG. 5A, the indications 0 mmHg to 100 mmHg are displayed between the lower side 500Fb as the first side corresponding to the low pressure side of the frame 500F and the upper side 500Fa as the second side corresponding to the high pressure side. Thus, the resolution of indication is improved for the size of the display screen 500. That is, if the size in the longitudinal direction of the frame 500F (corresponding to the size in the longitudinal direction of the display screen 500) is the same, the resolution of indication is improved about 3 times as compared with the case where the whole range from the minimum indication 0 mmHg to the maximum indication 300 mmHg is displayed simultaneously within the frame 500F. In contrast, if the resolution of indication has only to be the same in the case where the whole range from the minimum indication 0 mmHg to the maximum indication 300 mmHg is displayed simultaneously within the frame 500F, the size in the longitudinal direction of the frame 500F can be reduced.

More specifically, in this example, in order that pressure values (in the example in FIG. 5A, indication of "0 mmHg" and "100 mmHg") are displayed in the lower portion (place along the lower side 500Fb) and the upper portion (place along the upper side 500Fa) within the frame 500F, the pressure range indicated by the scale indication 501 displayed within the frame 500F is set to be wider than a range of 100 mmHg by a range of several mmHg, and is set to a range of 110 mmHg at most. Hereinafter, for simplicity, this is referred to as a range of 100 mmHg.

As shown in FIG. 1, in this example, on the front surface of the main body 10, the operation unit 52 includes a power switch 52A, a measurement start switch 52B, and a measurement stop switch 52C arranged on the right of the indicator 50, and includes a pressurization value setting volume 52D and a measurement mode changeover switch 52E arranged below the indicator 50. The power switch 52A is a switch for a user (including medical personnel such as a doctor and a nurse, a subject, and the like) to turn on/off the power supply of the sphygmomanometer 1 (it should be noted that in the following description, the power switch 52A is assumed to be turned on.) The measurement start switch 52B and the measurement stop switch 52C are switches for the user to instruct starting and stopping blood pressure measurement. The pressurization value setting volume 52D is a switch that allows the user to set the pressurization setting value (upper limit value) by the cuff 20 at the time of blood pressure measurement. The measurement mode changeover switch 52E is a switch for the user to switch and set the measurement mode of the sphygmomanometer 1. In this example, a mode in which the blood pressure value is automatically measured by the oscillometric method and a mode in which the user measures blood pressure using a stethoscope (the cuff 20 is pressurized and depressurized automatically) are assumed to be switchable. These switches 52A, 52B, 52C, 52D, and 52E input operation signals according to instructions by the user into the CPU 100.

Figure 2:
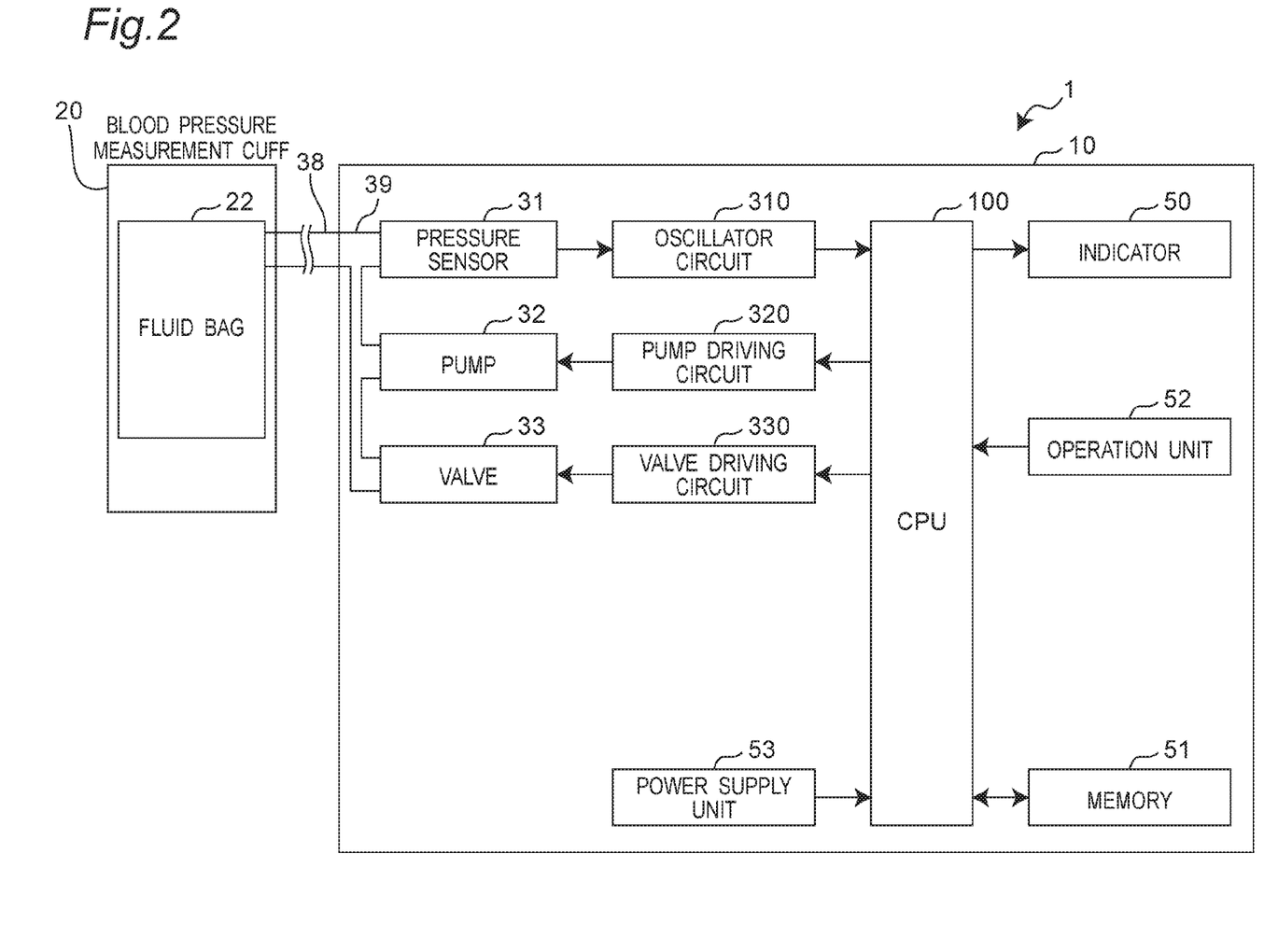
FIG. 2 is a diagram illustrating a block configuration of a control system of the sphygmomanometer.

As shown in FIG. 2, the main body 10 mounts, in addition to the indicator 50 and the operation unit 52 described above, a CPU 100, a memory 51, a power supply unit 53, a piezoresistive pressure sensor 31 for detecting the cuff pressure Pc, a pump 32 for supplying air as a fluid to the fluid bag 22, a valve 33 for adjusting the cuff pressure Pc by releasing the air to the external environment (at atmospheric pressure), an oscillator circuit 310 for converting the output from the pressure sensor 31 into a frequency, a pump driving circuit 320 for driving the pump 32, and a valve driving circuit 330 for driving the valve 33. The pressure sensor 31, the pump 32, and the valve 33 are connected to the fluid bag 22 contained in the cuff 20 via an air pipe 39 provided inside the main body and the air tube 38 communicating with the air pipe 39. Thus, air as a fluid flows between the pressure sensor 31, the pump 32, the valve 33, and the fluid bag 22.

The memory 51 stores a program for controlling the sphygmomanometer 1, setting data for setting various functions of the sphygmomanometer 1, and data on the measurement results of blood pressure values. In addition, the memory 51 is used as a work memory or the like when a program is executed.

The power supply unit 53 supplies electric power to each unit of the CPU 100, the pressure sensor 31, the pump 32, the valve 33, the indicator 50, the memory 51, the oscillator circuit 310, the pump driving circuit 320, and the valve driving circuit 330.

The oscillator circuit 310 oscillates based on an electrical signal value based on a change in electrical resistance due to the piezoresistive effect from the pressure sensor 31, and outputs a frequency signal having a frequency corresponding to the electrical signal value of the pressure sensor 31 to the CPU 100.

The CPU 100 operates as a pressure control unit according to a program for controlling the sphygmomanometer 1 stored in the memory 51, and performs control to drive the pump 32 via the pump driving circuit 320 and to drive the valve 33 via the valve driving circuit 330 in response to an operation signal from the operation unit 52. The valve 33 is opened and closed for discharging or sealing the air in the fluid bag 22 to control the cuff pressure Pc. In addition, the CPU 100 operates as a blood pressure calculation unit in the blood pressure measurement mode by the oscillometric method, and calculates the blood pressure value based on the signal from the pressure sensor 31. In addition, the CPU 100 controls the display contents of the indicator 50 as a display control unit and controls the memory 51.

Figure 3:
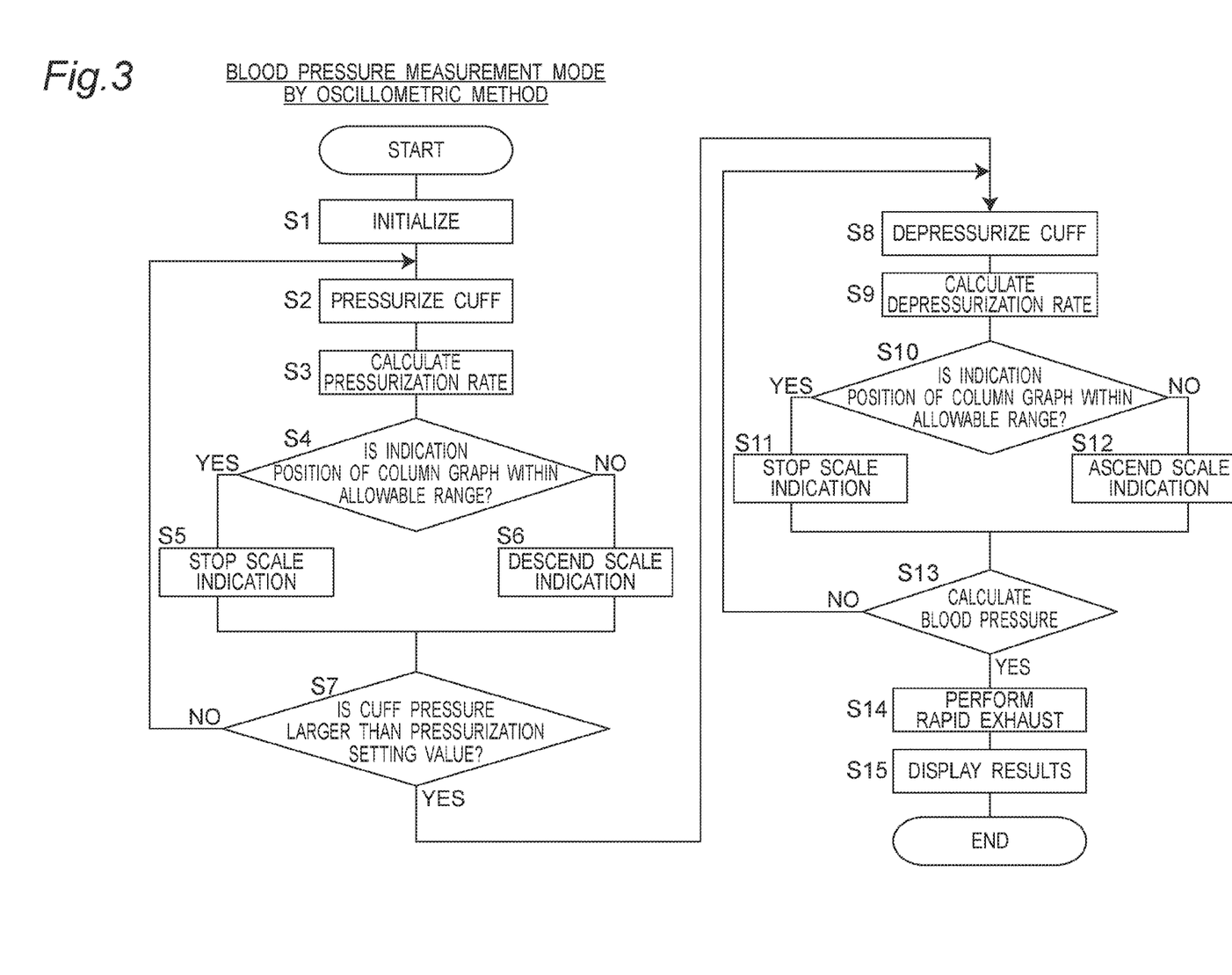
FIG. 3 is a diagram illustrating a flow of a blood pressure measurement mode by the oscillometric method in the sphygmomanometer.

FIG. 3 shows a flow of the blood pressure measurement mode by the oscillometric method in the sphygmomanometer 1 (in this example, it is assumed that the instruction is given by the measurement mode changeover switch 52E). Here, the display contents of the display screen 500 accompanying the blood pressure measurement will be described with reference to FIGS. 3 and 5 to 8. It should be noted that in measurement, the cuff 20 is previously wrapped around the measurement site (the upper arm in this example) of the subject.

i) When measurement start is instructed by the operation of the measurement start switch 52B, the sphygmomanometer 1 first performs initialization processing (step S1 in FIG. 3). That is, the CPU 100 initializes the processing memory region. In addition, the CPU 100 turns off the pump 32, opens the valve 33 to exhaust the air in the cuff 20 (fluid bag 22), and adjusts the pressure sensor 31 to 0 mmHg (sets the atmospheric pressure to 0 mmHg).

Figure 8A:
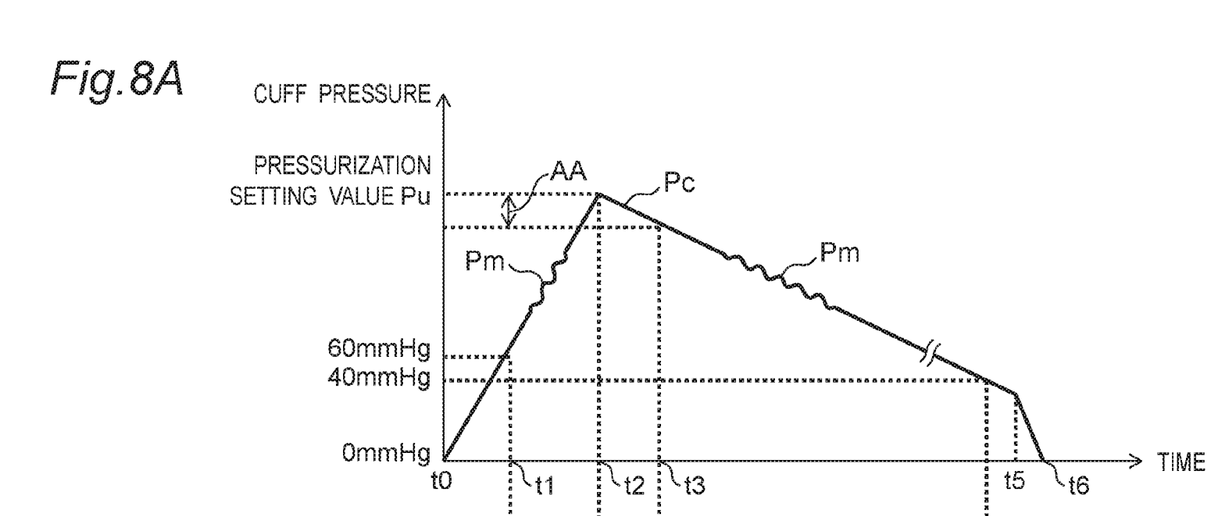
FIG. 8A is a diagram exemplifying a temporal change in cuff pressure accompanying blood pressure measurement with the sphygmomanometer.

At this time, the cuff pressure Pc is in the state at time t0 in FIG. 8A. In addition, as shown in FIG. 5A, the CPU 100 operates as a display control unit to cause the indicator 50 to indicate 0 mmHg being the current cuff pressure Pc. Specifically, as described above, as the scale indication 501 on the indicator 50, a range of 100 mmHg from 0 mmHg to 100 mmHg is indicated out of the displayable whole range (the range from the minimum indication 0 mmHg to the maximum indication 300 mmHg). The position of the top portion 502T of the column graph 502 with respect to the scale indication 501 indicates 0 mmHg being the current cuff pressure Pc.

ii) Next, the CPU 100 operates as a pressure control unit, closes the valve 33, drives the pump 32, and performs control to send air to the fluid bag 22 while observing the cuff pressure Pc with the pressure sensor 31. Thus, the fluid bag 22 is inflated and the cuff pressure Pc is gradually increased (step S2 in FIG. 3). The pressurization rate of the cuff pressure Pc is assumed to be set to a constant value within the range of 20 mmHg/sec to 30 mmHg/sec, for example.

Thus, as shown at times t0 to t1 in FIG. 8A, the cuff pressure Pc is pressurized at a constant pressurization rate in this example. In this pressurizing process, as shown in FIG. 5B, the CPU 100 operates as a display control unit to cause the indicator 50 to indicate the current cuff pressure Pc in real time. In the example in FIG. 5B, the position of the top portion 502T of the column graph 502 with respect to the scale indication 501 indicates about 45 mmHg.

iii) In addition, in this pressurizing process, the CPU 100 operates as a pressure change rate acquisition unit to acquire the pressurization rate as a pressure change rate obtained by actual measurement based on the output of the pressure sensor 31 (step S3 in FIG. 3). At this time, the CPU 100 removes from the actual pressure Pc of the cuff 20 the pressure fluctuation component Pm (see FIG. 8A) produced by the pulse wave occurred by the measurement site to obtain a steady pressurization rate at least for a certain period of time (typically for an initial period of one second to several seconds in the pressurizing process). It should be noted that a steady pressurization rate may be obtained sequentially over the whole period of the pressurizing process.

iv) In addition, during this pressurizing process, the CPU 100 operates as a display control unit to determine whether the position of the top portion 502T of the column graph 502 indicates the inside of a predetermined allowable range AA from the center of the scale indication 501 displayed within the frame 500F (step S4 in FIG. 3).

Figure 5C:
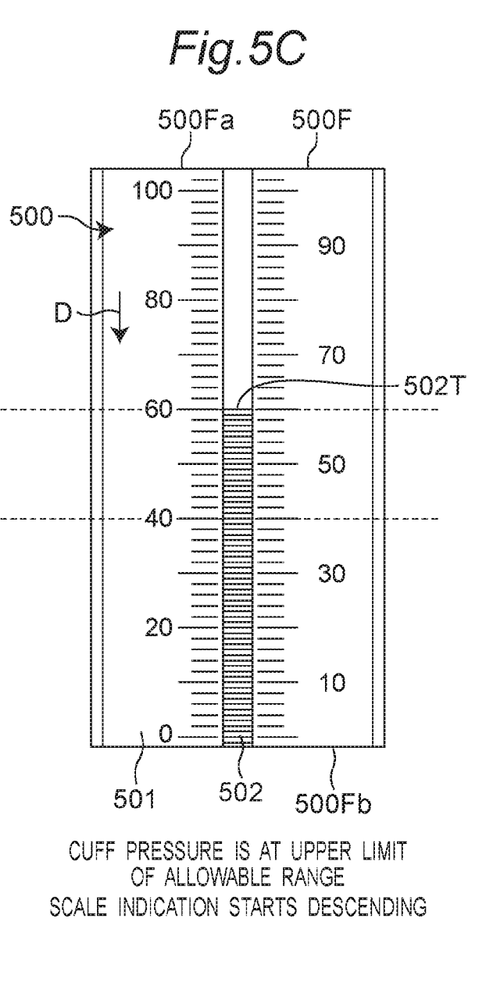
FIG. 5C is a diagram exemplifying a mode in which the display contents of the indicator of the sphygmomanometer change.

In this example, as shown in FIG. 5A, the allowable range AA is predetermined as a range of ±10 mmHg from the center of the scale indication 501 displayed within the frame 500F (it should be noted that as described below, even if the scale indication 501 slides in the longitudinal direction with respect to the frame 500F, the allowable range AA is determined as a range of ±10 mmHg from the center of the scale indication 501 actually displayed within the frame 500F, in other words, a range near the center with regard to the longitudinal direction of the frame 500F). That is, as illustrated in FIGS. 5A to 5C, when a range of 100 mmHg from 0 mmHg to 100 mmHg is indicated as the scale indication 501 in the indicator 50, the allowable range AA corresponds to a range from 40 mmHg to 60 mmHg (it should be noted that the display screen 500 does not display the broken lines indicating the upper and lower limits of the allowable range AA). Here, for example, in the state in FIG. 5B, the current cuff pressure Pc is about 45 mmHg, and therefore, the position of the top portion 502T of the column graph 502 indicates the inside of the allowable range AA. Thus, when the position of the top 502T of the column graph 502 indicates the inside of the allowable range AA (YES in step S4 in FIG. 3), the CPU100 operates as a display control unit to perform control to stop the scale indication 501 with respect to the frame 500F regardless of the change in the cuff pressure Pc (step S5 in FIG. 3). Thus, the user can easily read the value of the pressure Pc.

v) On the other hand, when the position of the top portion 502T of the column graph 502 does not indicate the inside of the allowable range AA (in other words, if it is about to deviate from the allowable range AA) (NO in step S4 in FIG. 3), the CPU100 operates as a display control unit to perform control to slide the scale indication 501 with respect to the frame 500F along the longitudinal direction (descend in this pressurizing process) at the slide speed corresponding to the pressurization rate obtained by actually measuring in step S3 so that the position of the top portion 502T of the column graph 502 falls within the allowable range AA (step S6 in FIG. 3). For example, if the above-described pressurization rate obtained by actually measuring the cuff pressure Pc is 25 mmHg/sec, the scale indication 501 is descended with the two left and right portions 501L and 501R being integrated, with respect to the frame 500F, at a slide speed corresponding to 25 mmHg/sec. Thus, it is possible to slide the scale indication 501 with respect to the frame 500F at an appropriate slide speed. In particular, it is possible to reduce the influence on the slide speed or position of the scale indication 501 with respect to the frame 500F due to the pressure fluctuation component Pm accompanying the pulse wave included in the cuff pressure Pc.

In this example, in this pressurizing process, it is assumed that the cuff pressure Pc reaches 60 mmHg at time t1 as shown in FIG. 8A. Accordingly, as shown in FIG. 5C, when the position of the top portion 502T of the column graph 502 reaches the upper limit (which corresponds to the indication 60 mmHg in the scale indication 501 actually displayed within the frame 500F) of the allowable range AA, the scale indication 501 starts descending with respect to the frame 500F as indicated by arrow D. Along with the descending of the scale indication 501, indications with larger values sequentially appear in (enter) the upper portion within the frame 500F (the place along the upper side 500Fa), while indications with smaller values sequentially disappear from (exit) the lower portion within the frame 500F (the place along the lower side 500Fb). The indications displayed within the frame 500F gradually ascend within the displayable whole range (the range from the minimum indication 0 mmHg to the maximum indication 300 mmHg) while maintaining a range of 100 mmHg as the range actually displayed.

During descending of the scale indication 501 with respect to the frame 500F in this pressurizing process, the position of the top portion 502T of the column graph 502 with respect to the frame 500F is basically maintained at the place at the upper limit of the allowable range AA. If the pressure fluctuation component Pm accompanying the pulse wave appears in the cuff pressure Pc, the position of the top portion 502T of the column graph 502 with respect to the frame 500F temporarily fluctuates from the place at the upper limit of the allowable range AA according to the pressure fluctuation component Pm.

Figure 8B:
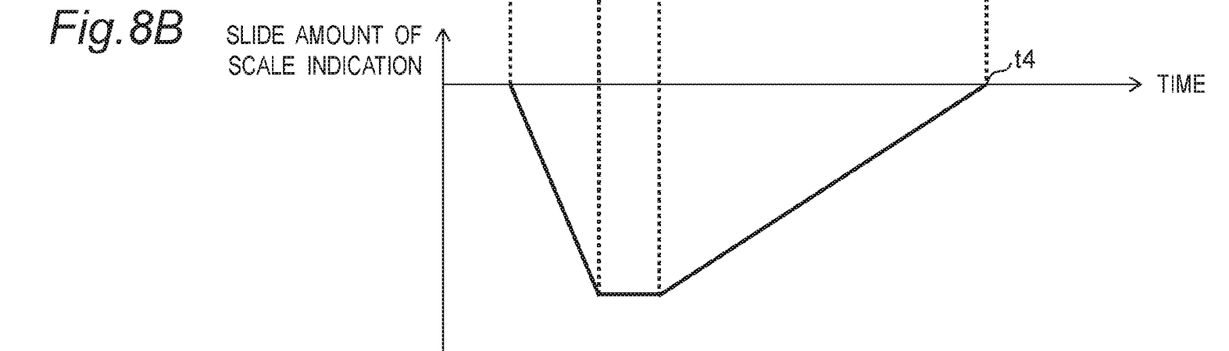
FIG. 8B is a diagram exemplifying a slide amount of the scale indication in the indicator accompanying a temporal change in cuff pressure.

In this way, as shown in FIG. 8B, the scale indication 501 is slid (descended) with respect to the frame 500F from time t1 to time t2 described below.

vi) Next, based on the output of the pressure sensor 31, the CPU 100 determines whether the cuff pressure Pc has become larger than the pressurization setting value Pu (step S7 in FIG. 3). In this example, the pressurization setting value Pu is assumed to be set to Pu=167 mmHg by the pressurization value setting volume 52D. It should be noted that the pressurization setting value Pu is recommended to be set to a value higher than the expected maximum blood pressure (systolic blood pressure) by 30 mmHg to 40 mmHg Here, if the cuff pressure Pc is not yet larger than the pressurization setting value Pu (NO in step S7 in FIG. 3), the process repeats the processes of steps S2 to S6 in FIG. 3. On the other hand, if the cuff pressure Pc becomes larger than the pressurization setting value Pu (in other words, if it is about to become larger) (YES in step S7 in FIG. 3), the CPU 100 operates as a pressure control unit to stop the pump 32 to stop pressurizing the cuff 20.

Figure 6A:
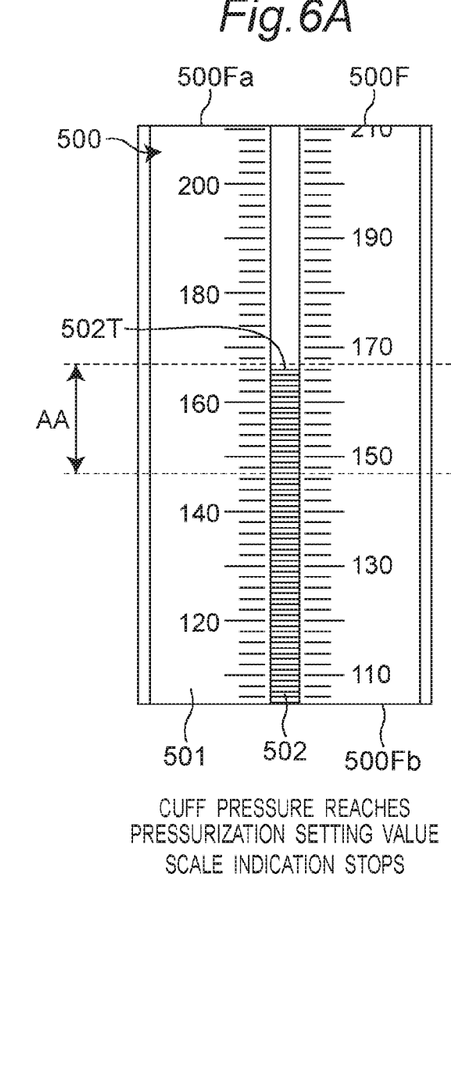
FIG. 6A is a diagram exemplifying a mode in which the display contents of the indicator of the sphygmomanometer change.

In this example, as shown in FIG. 8A, it is assumed that the cuff pressure Pc reaches the pressurization setting value Pu (=167 mmHg) at time t2 and the pressurization is stopped. Accordingly, as shown in FIG. 6A, the CPU 100 operates as a display control unit to stop the descending of the scale indication 501 with respect to the frame 500F. At this time, the position of the top portion 502T of the column graph 502 at the place at the upper limit of the allowable range AA indicates 167 mmHg in the scale indication 501.

vii) Next, the CPU 100 operates as a pressure control unit to perform control to open the valve 33 to discharge air from the fluid bag 22 while observing the cuff pressure Pc with the pressure sensor 31. Thus, the cuff pressure Pc is gradually decreased (step S8 in FIG. 3). The depressurization rate of the cuff pressure Pc is assumed to be set to a constant value within the range of 5 mmHg/sec to 8 mmHg/sec, for example.

Figure 6B:
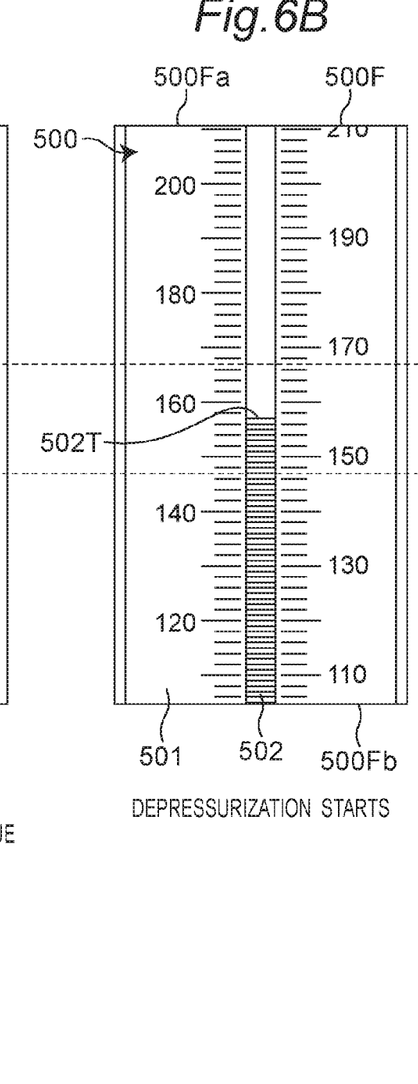
FIG. 6B is a diagram exemplifying a mode in which the display contents of the indicator of the sphygmomanometer change.

Thus, as shown at times t2 to t3 in FIG. 8A, the cuff pressure Pc is depressurized at a constant depressurization rate in this example. In this depressurizing process, as shown in FIG. 6B, the CPU 100 operates as a display control unit to cause the indicator 50 to indicate the current cuff pressure Pc in real time. In the example in FIG. 6B, the position of the top portion 502T of the column graph 502 with respect to the scale indication 501 indicates about 157 mmHg.

viii) In addition, in this depressurizing process, the CPU 100 operates as a pressure change rate acquisition unit to acquire the depressurization rate as a pressure change rate obtained by actual measurement based on the output of the pressure sensor 31 (step S9 in FIG. 3). At this time, the CPU 100 removes from the actual pressure Pc of the cuff 20 the pressure fluctuation component Pm (see FIG. 8A) produced by the pulse wave occurred by the measurement site to obtain a steady depressurization rate at least for a certain period of time (typically for an initial period of one second to several seconds in the depressurizing process). It should be noted that a steady depressurization rate may be obtained sequentially over the whole period of the depressurizing process.

ix) In addition, during this depressurizing process, the CPU 100 operates as a display control unit to determine whether the position of the top portion 502T of the column graph 502 indicates the inside of a predetermined allowable range AA from the center of the scale indication 501 displayed within the frame 500F (step S10 in FIG. 3).

Here, for example, in the state in FIG. 6B, the allowable range AA corresponds to a range from 147 mmHg to 167 mmHg. In addition, the current cuff pressure Pc is about 157 mmHg, and therefore, the position of the top portion 502T of the column graph 502 indicates the inside of the allowable range AA. Thus, when the position of the top portion 502T of the column graph 502 indicates the inside of the allowable range AA (YES in step S10 in FIG. 3), the CPU100 operates as a display control unit to perform control to stop the scale indication 501 with respect to the frame 500F regardless of the change in the cuff pressure Pc (step S11 in FIG. 3). Thus, the user can easily read the value of the pressure Pc.

In this way, as shown in FIG. 8B, the scale indication 501 is stopped with respect to the frame 500F from time t2 to time t3 described below.

x) On the other hand, when the position of the top portion 502T of the column graph 502 does not indicate the inside of the allowable range AA (in other words, if it is about to deviate from the allowable range AA) (NO in step S10 in FIG. 3), the CPU100 operates as a display control unit to perform control to slide the scale indication 501 with respect to the frame 500F along the longitudinal direction (ascend in this depressurizing process) at the slide speed corresponding to the depressurization rate obtained by actually measuring in step S9 so that the position of the top portion 502T of the column graph 502 falls within the allowable range AA (step S12 in FIG. 3). For example, if the above-described depressurization rate obtained by actually measuring the cuff pressure Pc is 6 mmHg/sec, the scale indication 501 is ascended with the two left and right portions 501L and 501R being integrated, with respect to the frame 500F, at a slide speed corresponding to 6 mmHg/sec. Thus, it is possible to slide the scale indication 501 with respect to the frame 500F at an appropriate slide speed. In particular, it is possible to reduce the influence on the slide speed or position of the scale indication 501 with respect to the frame 500F due to the pressure fluctuation component Pm accompanying the pulse wave included in the cuff pressure Pc.

Figure 6C:
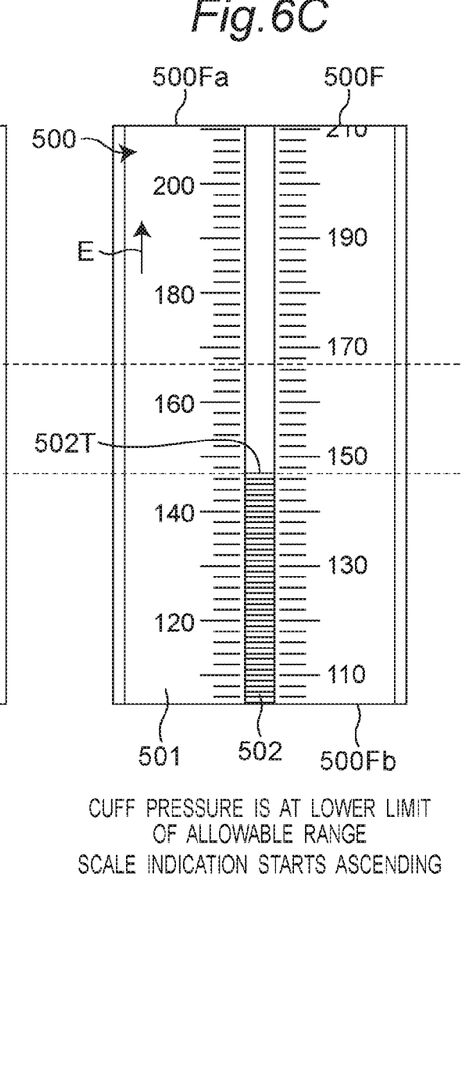
FIG. 6C is a diagram exemplifying a mode in which the display contents of the indicator of the sphygmomanometer change.

In this example, in this depressurizing process, as shown in FIG. 8A, at time t3, the cuff pressure Pc is assumed to have reached 147 mmHg (corresponding to the lower limit of the allowable range AA in the scale indication 501 actually displayed within the frame 500F). Accordingly, as shown in FIG. 6C, when the position of the top portion 502T of the column graph 502 reaches the lower limit of the allowable range AA, the scale indication 501 starts ascending with respect to the frame 500F as indicated by arrow E. Along with the ascending of the scale indication 501, indications with larger values sequentially disappear from (exit) the upper portion within the frame 500F (the place along the upper side 500Fa), while indications with smaller values sequentially appear in (enter) the lower portion within the frame 500F (the place along the lower side 500Fb). The indications displayed within the frame 500F gradually descend within the displayable whole range (the range from the minimum indication 0 mmHg to the maximum indication 300 mmHg) while maintaining a range of 100 mmHg as the range actually displayed.

During ascending of the scale indication 501 with respect to the frame 500F in this depressurizing process, the position of the top portion 502T of the column graph 502 with respect to the frame 500F is basically maintained at the place at the lower limit of the allowable range AA. If the pressure fluctuation component Pm accompanying the pulse wave appears in the cuff pressure Pc, the position of the top portion 502T of the column graph 502 with respect to the frame 500F temporarily fluctuates from the place at the lower limit of the allowable range AA according to the pressure fluctuation component Pm.

In this way, as shown in FIG. 8B, the scale indication 501 is slid (ascended) with respect to the frame 500F from time t3 to time t4 described below.

x) In this depressurizing process, the CPU 100 operates as a blood pressure calculation unit to attempt to calculate blood pressure values (systolic blood pressure and diastolic blood pressure) by a known oscillometric method based on the cuff pressure Pc (step S13 in FIG. 3). Here, if the blood pressure cannot be calculated yet due to lack of data (NO in step S13 in FIG. 3), the processes of steps S8 to S12 in FIG. 3 are repeated.

Figure 7A:
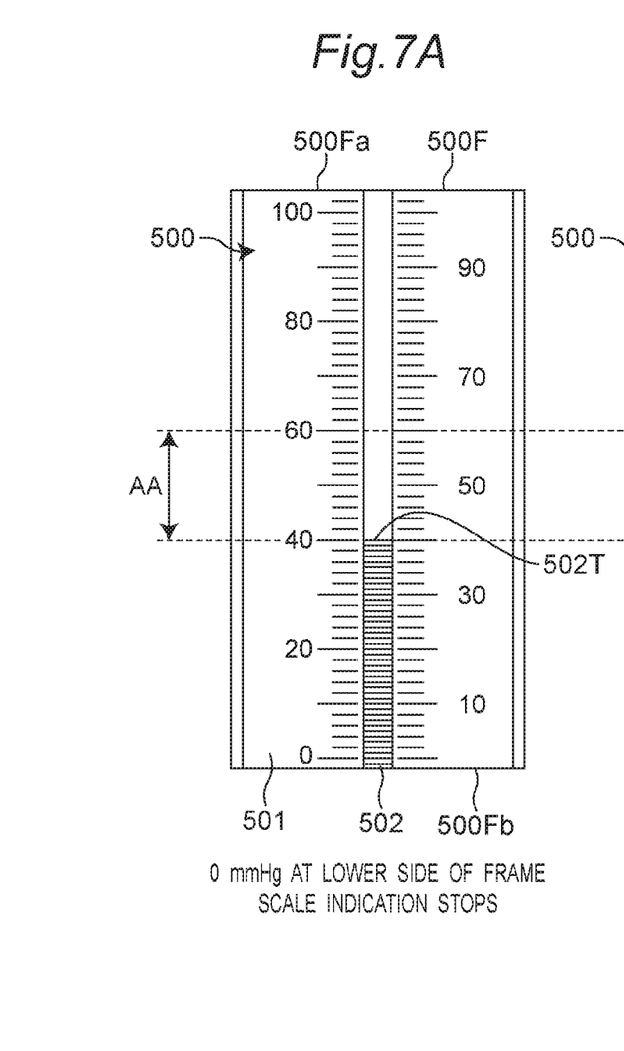
FIG. 7A is a diagram exemplifying a mode in which the display contents of the indicator of the sphygmomanometer change.
Figures 7B, 7C:
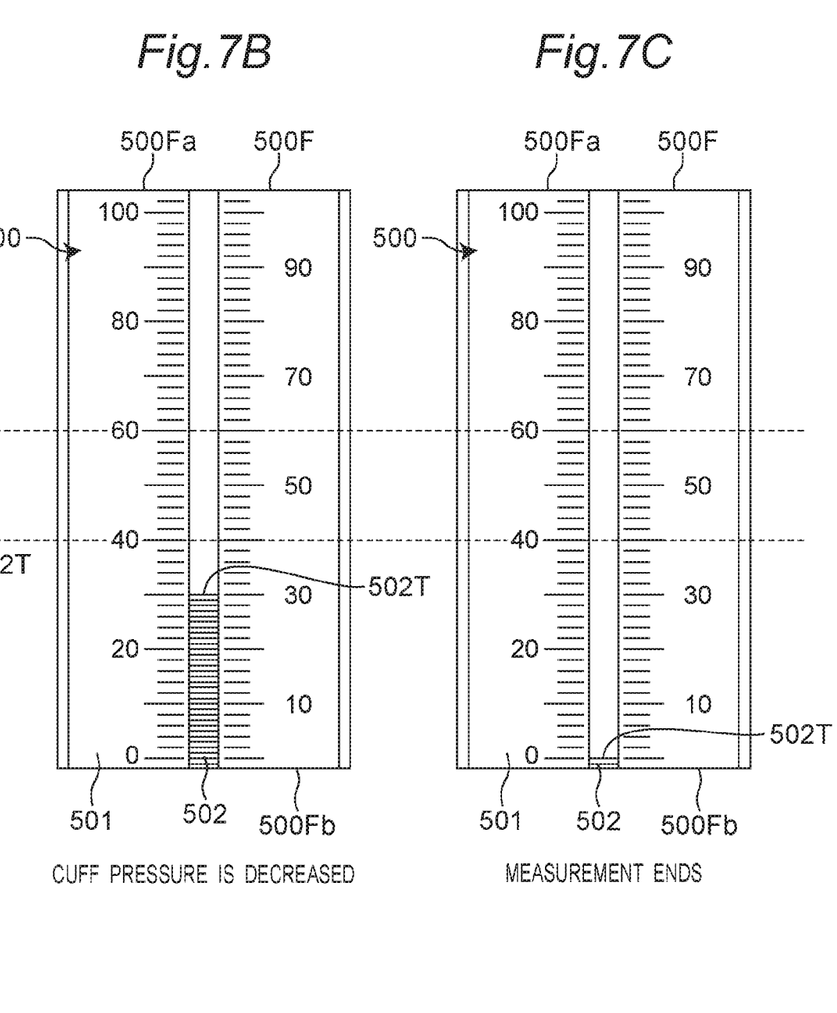
FIG. 7B is a diagram exemplifying a mode in which the display contents of the indicator of the sphygmomanometer change.
FIG. 7C is a diagram exemplifying a mode in which the display contents of the indicator of the sphygmomanometer change.

In this example, in this depressurizing process, as shown in FIG. 8A, the cuff pressure Pc reaches 40 mmHg at time t4, and along with this, as shown in FIG. 7A, the minimum indication 0 mmHg (in particular, the pressure indication of "0 mmHg" is included) of the scale indication 501 is assumed to have appeared in the lower portion (the place along the lower side 500Fb) within the frame 500F. Then, the CPU 100 operates as a display control unit to prohibit the minimum indication 0 mmHg from separating from the lower portion (the place along the lower side 500Fb) toward the upper side 500Fa within the frame 500F. That is, as shown in FIG. 8B, at time t4, the sliding of the scale indication 501 with respect to the frame 500F is stopped. Thereafter, even if the cuff pressure Pc drops below 40 mmHg, as shown in FIGS. 7B and 7C, the position of the scale indication 501 with respect to the frame 500F is maintained the same as that in FIG. 7A.

Thus, the scale indication 501 is restricted from sliding with respect to the frame 500F to an unnecessary range as the sphygmomanometer 1. Therefore, the usability is improved. For example, a user accustomed to using a traditional mercury column sphygmomanometer has a less sense of discomfort when using the sphygmomanometer 1.

xi) In the above-described depressurizing process, if the blood pressure values (systolic blood pressure and diastolic blood pressure) can be calculated (YES in step S13 in FIG. 3), the CPU 100 operates as a pressure control unit to fully open the valve 33 to perform rapid exhaust (step S14 in FIG. 3). For example, as shown in FIG. 8A, if the valve 33 is fully opened at time t5, the cuff pressure Pc rapidly decreases, and in this example, reaches the atmospheric pressure (0 mmHg) at time t6.

It should be noted that if blood pressures (systolic blood pressure and diastolic blood pressure) can be calculated at an early stage in the depressurizing process, the time at which rapid exhaust is started (in the above example, time t5) may precede the time at which the sliding (ascending) of the scale indication 501 with respect to the frame 500F is stopped (in the above example, time t4).

Thus, in this sphygmomanometer 1, when the cuff pressure Pc changes, the CPU 100 operates as a display control unit to slide the scale indication 501 with respect to the frame 500F at the slide speed corresponding to the pressure change rate obtained by actual measurement in the pressurizing process or the depressurizing process of the cuff 20 so that the column graph 502 falls within the frame 500F. Thus, the pressure Pc of the cuff 20 can be read corresponding to the position with respect to the scale indication 501 of the column graph 502 in a state where the column graph 502 falls within the frame 500F. In this way, the cuff pressure Pc is electronically displayed as a graph on the display screen 500. Therefore, the user can read the value of the cuff pressure Pc with an analog-like feeling similar to that when viewing a traditional mercury column sphygmomanometer. Moreover, in this sphygmomanometer 1, the pressure range indicated by the scale indication 501 within the frame 500F can be set as a partial range (in this example, a range of 100 mmHg to 110 mmHg) within the whole range that can be displayed by sliding (for example, a range from the minimum indication 0 mmHg to the maximum indication 300 mmHg which is the same as that of the traditional mercury column sphygmomanometer). In that case, the resolution of indication can be improved for the size of the display screen 500 (corresponding to the size of the frame 500F) with regard to the sliding direction of the scale indication 501.

xii) In the blood pressure measurement mode by the oscillometric method, after starting rapid exhaust (step S14 in FIG. 3), the CPU100 causes the indicator 50 to digitally indicate the measured systolic blood pressure (maximum blood pressure), diastolic blood pressure (minimum blood pressure), and pulse rate, for example, as shown in Table 1 below (step S15 in FIG. 3), instead of the analog-like display screen 500 having substantially the same appearance as in a traditional mercury column sphygmomanometer, or in addition to the analog-like display screen 500. Thus, the user can know the measured blood pressure value and pulse rate in numerical values.

TABLE 1

| Maximum blood pressure | 125 mmHg |
| Minimum blood pressure | 80 mmHg |
| Pulse rate | 60 beats/minute |

In the above example, in order to facilitate understanding, it is described that in the depressurizing process of steps S8 to S12 in FIG. 3, the CPU 100 operates as the display control unit for the first time to prohibit the minimum indication 0 mmHg from separating from the lower portion (the place along the lower side 500Fb) toward the upper side 500Fa within the frame 500F as shown in FIGS. 7A to 7C. However, actually, even in the pressurizing process of steps S2 to S7 in FIG. 3, the CPU 100 operates as the display control unit to prohibit the minimum indication 0 mmHg from separating from the lower portion (the place along the lower side 500Fb) toward the upper side 500Fa within the frame 500F as shown in FIGS. 5A to 5C. Thus, the scale indication 501 is restricted from sliding with respect to the frame 500F to an unnecessary range as the sphygmomanometer 1.

Figure 9:
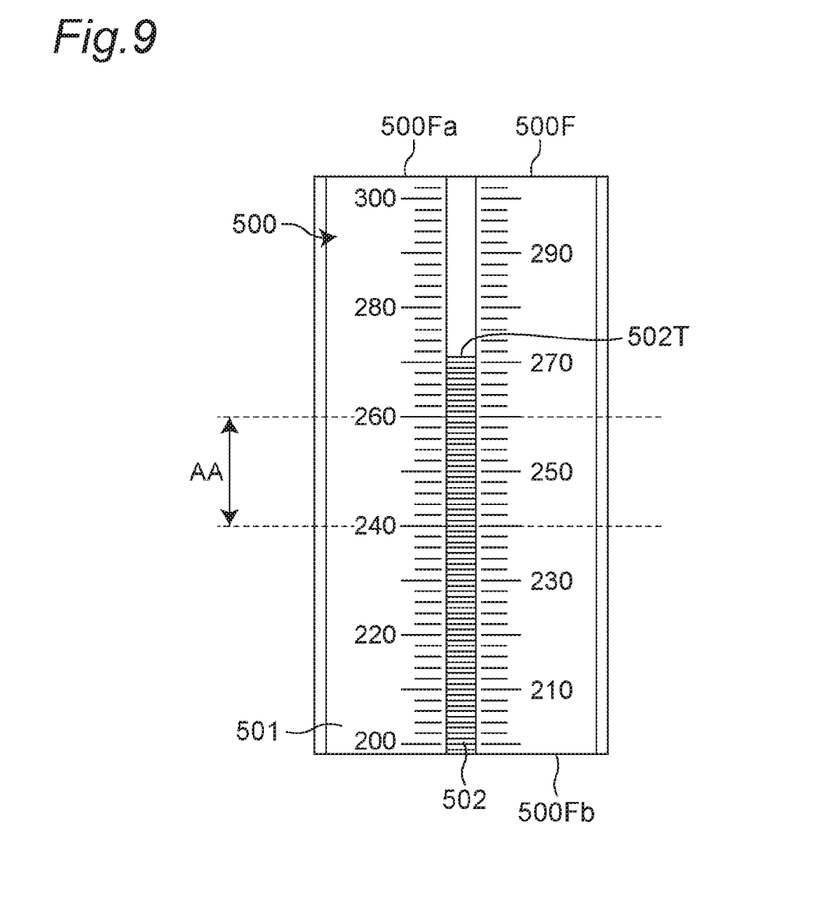
FIG. 9 is a diagram exemplifying the display contents of the indicator of the sphygmomanometer when the cuff pressure ascends to 260 mmHg or more.

In addition, if the cuff pressure Pc ascends to 260 mmHg or more, for example, as shown in FIG. 9 (in the example in FIG. 9, the cuff pressure Pc reaches 271 mmHg), the scale indication 501 with respect to the frame 500F slides (descends), and the maximum indication 300 mmHg (in particular, the pressure indication of "300 mmHg" is included) appears in the upper portion (the place along the upper side 500Fa) within the frame 500F. Also in that case, the CPU 100 operates as a display control unit to prohibit the maximum indication 300 mmHg from separating from the upper portion (the place along the upper side 500Fa) toward the lower side 500 Fb within the frame 500F. Thus, the scale indication 501 is restricted from sliding with respect to the frame 500F to an unnecessary range as the sphygmomanometer 1. Therefore, the usability is improved. For example, a user accustomed to using a traditional mercury column sphygmomanometer has a less sense of discomfort when using the sphygmomanometer 1.

In addition, in the above example, in step S7 in FIG. 3, the pressurization setting value Pu is assumed to be set to Pu=167 mmHg by the pressurization value setting volume 52D. However, the present disclosure is not limited thereto. For example, it is assumed that the blood pressure value (systolic blood pressure) obtained in the previous blood pressure measurement is stored in the memory 51. Then, at the time of the blood pressure measurement this time, the CPU 100 may read the blood pressure value (systolic blood pressure) from the memory 51, and the value obtained by adding, for example, 40 mmHg to the blood pressure value (systolic blood pressure) may be used as the pressurization setting value Pu.

Instead, the CPU 100 may use a fixed value such as 200 mmHg as the pressurization setting value Pu.

In addition, in the above example, in steps S6 and S12 in FIG. 3, when sliding the scale indication 501 with respect to the frame 500F, the CPU 100 is assumed to slide the scale indication 501 at a slide speed corresponding to the pressure change rate obtained by actual measurement in the pressurizing process or the depressurizing process of the cuff 20. However, the present disclosure is not limited thereto. For example, in a case where the pressure change rate in the pressurizing process or the depressurizing process is known, when the scale indication 501 is slid with respect to the frame 500F, the CPU 100 may slide the scale indication 501 at a slide speed corresponding to the pressure change rate. In that case, there is an advantage that the processing of the CPU 100 can be simplified.

Figure 4:
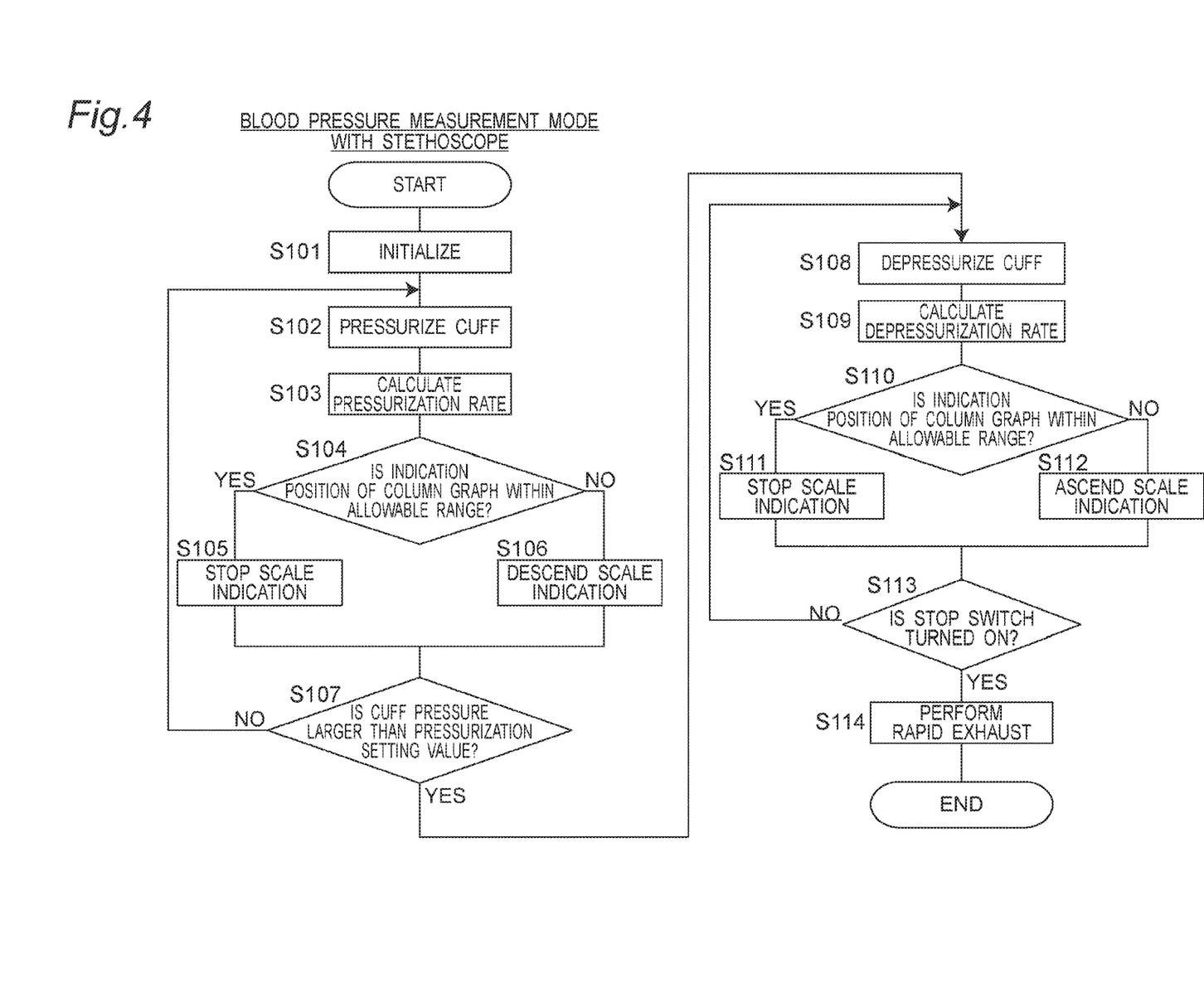
FIG. 4 is a diagram illustrating a flow of a blood pressure measurement mode with a stethoscope in the sphygmomanometer.

FIG. 4 shows a flow of the blood pressure measurement mode with a stethoscope in the sphygmomanometer 1 (in this example, it is assumed that the instruction is given by the measurement mode changeover switch 52E). In the blood pressure measurement mode by the oscillometric method described above, the CPU 100 operates as a blood pressure calculation unit to calculate blood pressure values (systolic blood pressure and diastolic blood pressure) (step S13 in FIG. 3). Instead, the blood pressure measurement mode with the stethoscope is different from the blood pressure measurement mode by the oscillometric method in that the user (for example, a doctor) measures blood pressure values (systolic blood pressure and diastolic blood pressure) with a stethoscope.

Specifically, the CPU 100 proceeds to steps S101 to S112 in FIG. 4 in the same manner as steps S1 to S12 in FIG. 3. Even in the blood pressure measurement mode with the stethoscope, when the cuff pressure Pc changes, the CPU 100 operates as a display control unit to slide the scale indication 501 with respect to the frame 500F at the slide speed corresponding to the pressure change rate obtained by actual measurement in the pressurizing process or the depressurizing process of the cuff 20 so that the column graph 502 falls within the frame 500F. Thus, the pressure Pc of the cuff 20 can be read corresponding to the position with respect to the scale indication 501 of the column graph 502 in a state where the column graph 502 falls within the frame 500F. In this way, the cuff pressure Pc is electronically displayed as a graph on the display screen 500.

Then, in the depressurizing process (steps S108 to S112 in FIG. 4), the user listens to the Korotkoff sound occurred by the measurement site with the stethoscope, and visually reads the cuff pressure Pc displayed on the display screen 500 at the timings of appearance and disappearance of the Korotkoff sound. Thus, the blood pressure values (systolic blood pressure and diastolic blood pressure) are measured. At this time, the user can read the value of the cuff pressure Pc with an analog-like feeling similar to that when viewing a traditional mercury column sphygmomanometer.

When the reading of the cuff pressure Pc is completed, the user presses the measurement stop switch 52C (step S113 in FIG. 4). If the measurement stop switch 52C is pressed (YES in step S113 in FIG. 4), the CPU 100 operates as a pressure control unit to fully open the valve 33 to perform rapid exhaust (step S114 in FIG. 4). Thereafter, the digital display corresponding to step S15 in FIG. 3 is not performed.

The blood pressure measurement mode with the stethoscope is suitable for users accustomed to measuring blood pressure values with the stethoscope.

In both of the examples of the flows in FIGS. 3 and 4 above, the CPU 100 operates as a pressure control unit to control the pump 32 and the valve 33 to increase or decrease the cuff pressure Pc. However, the present disclosure is not limited thereto. Instead of the pump 32 and the valve 33, a traditional rubber ball (including an exhaust valve) may be attached to the cuff 20 via an air tube, and the cuff pressure Pc may be manually increased or decreased. In that case, the sense of discomfort in using the sphygmomanometer 1 becomes smaller for a user accustomed to using the traditional mercury column sphygmomanometer.

In addition, in the above example, it is assumed that on the display screen 500, the scale indication 501 and the column graph 502 as a mark are displayed along the longitudinal direction and are slidable along the longitudinal direction. However, the present disclosure is not limited thereto. For example, on the display screen 500, a scale indication that makes the value of the cuff pressure Pc readable, and a band graph as a mark that represents the cuff pressure Pc by its position with respect to the scale indication 501 may be displayed in the horizontal direction and may be slidable along the horizontal direction. In addition, the mark is not limited to the column graph or the band graph, and may be a mark such as an arrow pointing a specific indication of the scale indication.

In addition, in the above example, the indicator 50 includes an LCD, but the indicator 50 is not limited thereto. The indicator 50 has only to be a display capable of slidably displaying a scale indication and a mark such as a column graph on the display screen, such as an electroluminescence (EL) display.

As described above, a sphygmomanometer according to the present disclosure is a sphygmomanometer electronically displaying as a graph a pressure of a blood pressure measurement cuff pressing a measurement site on a display screen, the sphygmomanometer comprising:
- a frame that spatially demarcates a region in which the display screen is displayed;
- a scale indication displayed along one direction on the display screen so as to make a value of pressure readable;
- a mark displayed on the display screen so as to represent a pressure of the cuff by a position of the mark with respect to the scale indication; and
- a display control unit configured to perform control to slide the scale indication with respect to the frame along the one direction at a slide speed corresponding to a predetermined pressure change rate or a pressure change rate obtained by actual measurement in a pressurizing process or a depressurizing process of the cuff so that the mark falls within the frame when the pressure changes.

Here, the "predetermined pressure change rate" means that, for example, when the pressure change rate in the pressurizing process or the depressurizing process is known, a slide speed corresponding to the pressure change rate is used. The "pressure change rate obtained by actual measurement in the pressurizing process or the depressurizing process" of the cuff typically means obtaining the pressure change rate by actual measurement in the initial stage of the pressurizing process or the depressurizing process, and using a slide speed corresponding to the pressure change rate.

In the sphygmomanometer of this disclosure, a scale indication for making a value of the cuff pressure readable is displayed along one direction on the display screen. In addition, a mark indicating the pressure of the cuff by its position with respect to the scale indication is displayed on the display screen. When the pressure of the blood pressure measurement cuff changes, the display control unit performs control to slide the scale indication with respect to the frame along the one direction at a slide speed corresponding to a predetermined pressure change rate or a pressure change rate obtained by actual measurement in a pressurizing process or a depressurizing process of the cuff so that the mark falls within the frame. Thus, the pressure of the cuff can be read corresponding to the position of the mark with respect to the scale indication in a state where the mark falls within the frame. In this way, the cuff pressure is electronically displayed as a graph on the display screen. Therefore, a user (including medical personnel such as a doctor and a nurse, a subject, and the like) can read the pressure value with an analog-like feeling similar to that when viewing a traditional mercury sphygmomanometer. Moreover, in this sphygmomanometer, the pressure range indicated by the scale indication within the frame can be set as a partial range within the whole range that can be displayed by sliding (for example, a range from the minimum indication 0 mmHg to the maximum indication 300 mmHg which is the same as that of the traditional mercury column sphygmomanometer). In that case, the resolution of indication can be improved for the size of the display screen (corresponding to the size of the frame) with regard to the sliding direction of the scale indication.

In the sphygmomanometer according to one embodiment, when the mark indicates an inside of a predetermined allowable range from a center of the scale indication displayed within the frame, the display control unit performs control to stop the scale indication with respect to the frame regardless of a change in the pressure.

When the mark indicates an inside of a predetermined allowable range from a center of the scale indication displayed within the frame, there is little need to slide the scale indication. Thus, in the sphygmomanometer of this one embodiment, when the mark indicates an inside of a predetermined allowable range from a center of the scale indication within the frame, the display control unit performs control to stop the scale indication with respect to the frame regardless of a change in the pressure. Thus, the user can easily read the value of the pressure.

The sphygmomanometer according to one embodiment further comprises a pressure change rate acquisition unit configured to remove from the pressure of the cuff a pressure fluctuation component produced by a pulse wave occurred by the measurement site to obtain a steady pressure change rate at least for a certain period of time as the pressure change rate obtained by the actual measurement.

Here, the "certain period of time" typically refers to an initial period of one second to several seconds in the pressurizing process or the depressurizing process. However, the pressure change rate acquisition unit may sequentially obtain a steady pressure change rate as the pressurizing process or the depressurizing process progresses.

In the sphygmomanometer of this one embodiment, the pressure change rate acquisition unit removes from the pressure of the cuff a pressure fluctuation component produced by a pulse wave occurred by the measurement site to obtain a steady pressure change rate at least for a certain period of time as the pressure change rate obtained by the actual measurement. The display control unit slides the scale indication with respect to the frame at a slide speed corresponding to the pressure change rate. Thus, the scale indication can be slid at an appropriate slide speed with respect to the frame so that the mark falls within the frame. In particular, it is possible to reduce the influence on the slide speed or position of the scale indication with respect to the frame due to the pressure fluctuation component produced by the pulse wave included in the pressure of the cuff.

It should be noted that if the pressure fluctuation component produced by the pulse wave occurred by the measurement site is not removed from the pressure of the cuff, and the scale indication is slid with respect to the frame while directly corresponding to the pressure change rate of the cuff, the slide speed of the scale indication with respect to the frame fluctuates in a short time, or the position of the scale indication moves up and down in a short time due to the pressure fluctuation component produced by the pulse wave. Therefore, this results in giving a sense of discomfort to the user viewing the display screen.

In the sphygmomanometer according to one embodiment,
- the scale indication is displayed along a longitudinal direction as the one direction on the display screen,
- the mark is a column graph extending in the longitudinal direction along the scale indication, and
- the display control unit slides the scale indication along the longitudinal direction.

In the sphygmomanometer of this one embodiment, external appearance of the display screen is substantially the same as that of a traditional mercury column sphygmomanometer. Therefore, a user accustomed to using the traditional mercury column sphygmomanometer has a less sense of discomfort when using the sphygmomanometer.

The sphygmomanometer according to one embodiment further comprises:
  a pressure control unit configured to supply air to the cuff or discharge air from the cuff to control the pressure; and
  a blood pressure calculation unit configured to calculate blood pressure by an oscillometric method based on the pressure of the cuff in a pressurizing process or a depressurizing process of the cuff.

In the sphygmomanometer of this one embodiment, the pressure control unit controls the pressure by supplying air to the cuff or discharging air from the cuff. Along with this, the blood pressure calculation unit calculates blood pressure by the oscillometric method based on the pressure of the cuff in the pressurizing process or the depressurizing process of the cuff. Therefore, the blood pressure value can be automatically measured.

It should be noted that instead of that, for example, a doctor may apply a stethoscope to the measurement site of the subject while viewing the display screen of the sphygmomanometer and measure the blood pressure by stethoscopy.

In the sphygmomanometer according to one embodiment, a pressure range indicated by the scale indication displayed within the frame corresponds to a range of 100 mmHg to 110 mmHg being a part within a range from a minimum indication 0 mmHg to a maximum indication 300 mmHg.

In the sphygmomanometer of this one embodiment, the resolution of indication is improved for the size of the display screen. That is, if the size of the frame with regard to the slide direction of the scale indication (corresponding to the size of the display screen) is the same, the resolution of indication is improved about 3 times as compared with the case where the whole range from the minimum indication 0 mmHg to the maximum indication 300 mmHg is displayed simultaneously within the frame. In contrast, if the resolution of indication with regard to the slide direction of the scale indication has only to be the same, the size of the frame with regard to the slide direction of the scale indication can be reduced.

It should be noted that if the pressure range indicated by the scale indication displayed within the frame is wider than, for example, a range of 150 mmHg, the resolution of indication cannot be sufficiently improved. On the other hand, if the pressure range indicated by the scale indication within the frame is narrower than, for example, a range of 50 mmHg, the pressure fluctuation component accompanying the pulse wave included in the pressure of the cuff within the display screen looks too large, making it rather difficult to use.

In the sphygmomanometer according to one embodiment, between a first side corresponding to a lower pressure side and a second side corresponding to a higher pressure side of the scale indication of two sides facing each other of the frame, the display control unit performs control to restrict a range in which the scale indication slides with respect to the frame by prohibiting a minimum indication 0 mmHg from separating from a place along the first side toward the second side, and by prohibiting a maximum indication 300 mmHg from separating from a place along the second side toward the first side.

In the sphygmomanometer of this one embodiment, the scale indication is restricted from sliding with respect to the frame to an unnecessary range as the sphygmomanometer. Therefore, the usability is improved. For example, a user accustomed to using a traditional mercury column sphygmomanometer has a less sense of discomfort when using the sphygmomanometer.

As is apparent from the above, according to the sphygmomanometer of this disclosure, the pressure of the blood pressure measurement cuff can be electronically displayed as a graph on the display screen, and furthermore the resolution of indication can be improved.

The above embodiment is an exemplary, and various modifications can be made without departing from the scope of the present disclosure. Each of the above embodiments can be implemented independently, but combinations of the embodiments are also possible. In addition, various features in different embodiments can also be independently implemented, but combinations of features in different embodiments are also possible.

The invention claimed is:

1. A sphygmomanometer configured to electronically display, on a display screen, a graph of a pressure measured from a blood pressure measurement cuff pressing a measurement site;
  a frame that spatially demarcates the display screen; and
  a processor,
  wherein the processor is configured to create a scale indication including scale values over a full range of blood pressure measurement by the sphygmomanometer, to select only a partial range of the scale indication as a display target range that has an upper bound and a lower bound, and to display the display target range along one direction of the display screen,
  wherein the processor is further configured to create a mark to be displayed on the display screen, and to represent the pressure of the blood pressure measurement cuff by a position of the mark relative to the scale indication,
  wherein the processor is further configured to set a slide speed for translationally moving the display target range in a direction in which the scale values increase or decrease in magnitude along the scale indication while keeping a space between the upper bound and the lower bound constant, and
  wherein the processor is further configured to act as a display control unit to put the position of the mark within the display screen, by selecting the display target range in the scale indication while, by the slide speed, translationally moving the display target range in the direction in which the scale values increase or decrease in magnitude along the scale indication while keeping the space between the upper bound and the lower bound constant, as the pressure of the blood pressure measurement cuff changes during the blood pressure measurement.

2. The sphygmomanometer according to claim 1, wherein when acting as the display control unit, the processor is further configured:
  to determine, as the pressure of the blood pressure measurement cuff changes during the blood pressure measurement, whether a new position of the mark would fall, with respect to the one direction, within a predetermined allowable range from a center position of the display target range displayed within the display screen; and when determined that the new position of the mark would fall within the predetermined allowable range, to perform control to stop translational moving of the display target range along the scale indication so as to maintain the selecting of the display target range in the scale indication regardless of any change of the pressure of the blood pressure measurement cuff, such that the new position of the mark is allowed to move in the one direction within the predetermined allowable range of the display target range displayed within the display screen.

3. The sphygmomanometer according to claim 1, wherein the scale indication is displayed along a longitudinal direction of the display screen, the mark is a column graph extending in the longitudinal direction along the scale indication, and by the processor acting as the display control unit, a position of a top portion of the column graph is put within the display screen.

4. The sphygmomanometer according to claim 1, wherein the processor is further configured to act as a pressure control unit to supply air to the blood pressure measurement cuff or discharge air from the blood pressure measurement cuff to control the pressure; and the processor is further configured to act as a blood pressure calculation unit to calculate blood pressure by an oscillometric method based on the pressure of the blood pressure measurement cuff in a pressurizing process or a depressurizing process of the blood pressure measurement cuff.

5. The sphygmomanometer according to claim 1, wherein the full range of the blood pressure measurement is 0 mmHg to 300 mmHg, and the display target range is one-third range of the full range of the blood pressure measurement.

6. The sphygmomanometer according to claim 1, wherein when acting as the display control unit, the processor is further configured to restrict the display target range from being selected beyond 300 mmHg or below 0 mmHg.

7. The sphygmomanometer according to claim 1, wherein the scale indication includes:

an axis to be displayed on the display screen in a manner extending along the one direction, and the scale values attached to the axis.

8. The sphygmomanometer according to claim 1, wherein the processor is configured to set the slide speed to correspond to a predetermined first pressure change rate for the blood pressure measurement cuff during the blood pressure measurement.

9. The sphygmomanometer according to claim 1, wherein the processor is further configured to act as a pressure change rate acquisition unit to identify, for a partial period of time in a pressurizing process or a depressurizing process of the blood pressure measurement cuff during the blood pressure measurement, a pressure fluctuation component that is produced by a pulse wave at the measurement site and is contained in a pressure signal measured from the blood pressure measurement cuff, and then to remove the pressure fluctuation component from the pressure signal so as to obtain a second pressure change rate by an actual measurement, and the processor is configured to set the slide speed to correspond to the second pressure change rate.

* * * * *